United States Patent
Walter et al.

(10) Patent No.: US 8,371,744 B2
(45) Date of Patent: Feb. 12, 2013

(54) MIXER AND SYSTEM FOR MIXING AND DISPENSING A MATERIAL

(75) Inventors: Alexander Walter, Pürgen (DE); Jens Gramann, Gräfelfing (DE); Manfred Harre, Landsberg am Lech (DE); Marc Peuker, Schöndorf (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 13/392,561

(22) PCT Filed: Aug. 23, 2010

(86) PCT No.: PCT/US2010/046357
§ 371 (c)(1),
(2), (4) Date: May 14, 2012

(87) PCT Pub. No.: WO2011/031440
PCT Pub. Date: Mar. 17, 2011

(65) Prior Publication Data
US 2012/0218856 A1      Aug. 30, 2012

(30) Foreign Application Priority Data
Aug. 28, 2009   (GB) .................................. 0915007.9

(51) Int. Cl.
*B01F 7/00*       (2006.01)
*B67D 7/74*       (2010.01)
(52) U.S. Cl. .................. 366/331; 366/172.1; 222/145.6
(58) Field of Classification Search ............... 366/171.1, 366/172.1–173.2, 176.1, 181.5, 189, 331; 403/359.1, 359.3, 359.4, 359.6, 360, 24; 222/145.5, 145.6, 325–327
See application file for complete search history.

(56) References Cited

U.S. PATENT DOCUMENTS

| | | | | |
|---|---|---|---|---|
| 2,833,576 A * | 5/1958 | Cirone | .......................... | 403/334 |
| 2,869,907 A * | 1/1959 | Deliso | ......................... | 403/359.6 |
| 2,893,769 A * | 7/1959 | Deliso | ......................... | 403/359.6 |
| 3,226,093 A * | 12/1965 | Gugel et al. | .................. | 366/290 |
| 3,290,918 A * | 12/1966 | Weasler | .......................... | 72/340 |
| 3,485,520 A * | 12/1969 | Alexander | .................... | 403/334 |
| 3,542,178 A | 11/1970 | Ripple | | |
| 4,185,388 A * | 1/1980 | Jarby | ............................ | 433/125 |

(Continued)

FOREIGN PATENT DOCUMENTS

AT   332 527   10/1976
DE   93 13 604   1/1994

(Continued)

OTHER PUBLICATIONS

International Search Report for International Publication No. PCT/US2010/046357, dated Dec. 14, 2010.

*Primary Examiner* — Charles E Cooley
(74) *Attorney, Agent, or Firm* — Carlos M. Téllez (57) ABSTRACT

A mixer for mixing at least two-components of a dental material comprises a mixing rotor with a coupling for coupling with a drive shaft for driving the mixing rotor. Further a device for dispensing at least two components of a dental material comprises a drive shaft for driving a mixing rotor of a mixer. The coupling of the mixer and/or the device comprises at least one guiding ridge which preferably facilitates coupling to the drive shaft.

11 Claims, 6 Drawing Sheets

U.S. PATENT DOCUMENTS

| | | | |
|---|---|---|---|
| 4,832,573 A * | 5/1989 | Dorski | 416/241 A |
| 4,832,637 A * | 5/1989 | Goluba | 440/83 |
| 5,366,286 A * | 11/1994 | Ruttimann | 366/129 |
| 5,402,710 A * | 4/1995 | Chen | 99/348 |
| 6,244,740 B1 | 6/2001 | Wagner | |
| 6,439,760 B1 * | 8/2002 | Langeloh et al. | 366/206 |
| 6,443,612 B1 * | 9/2002 | Keller | 366/307 |
| 6,837,612 B2 | 1/2005 | Bublewitz | |
| 6,932,243 B2 * | 8/2005 | Keller | 222/145.6 |
| 7,387,462 B2 * | 6/2008 | Hacker | 403/359.6 |
| 7,972,057 B2 * | 7/2011 | Meyer et al. | 366/172.1 |
| 8,147,122 B2 * | 4/2012 | Pieroni | 366/171.1 |
| 2002/0175186 A1 * | 11/2002 | Keller | 222/145.6 |
| 2004/0257909 A1 * | 12/2004 | Pieroni | 366/172.1 |
| 2006/0071023 A1 * | 4/2006 | Lein et al. | 222/135 |
| 2008/0056061 A1 * | 3/2008 | Pauser et al. | 366/152.2 |
| 2009/0279382 A1 * | 11/2009 | Harre et al. | 366/133 |
| 2010/0091607 A1 * | 4/2010 | Meyer et al. | 366/151.2 |
| 2012/0218856 A1 * | 8/2012 | Walter et al. | 366/307 |

FOREIGN PATENT DOCUMENTS

| | | |
|---|---|---|
| DE | 200 16 245 | 5/2001 |
| EP | 1 458 467 | 5/2008 |
| GB | 2 113 352 | 8/1983 |
| WO | WO 9843727 A1 * | 10/1998 |
| WO | WO 03/055582 | 7/2003 |
| WO | WO 2007/106701 | 9/2007 |
| WO | WO 2011/031440 | 3/2011 |

* cited by examiner

MIXER AND SYSTEM FOR MIXING AND DISPENSING A MATERIAL

CROSS-REFERENCE TO RELATED APPLICATIONS

This application is a national stage filing under 35 U.S.C. 371 of PCT/US2010/046357, filed Aug. 23, 2010, which claims priority to Great Britain Patent Application No. 0915007.9, filed Aug. 28, 2009, the disclosures of which are herein incorporated by reference in their entirety.

FIELD OF THE INVENTION

The invention relates to a mixer for use with a device for mixing and dispensing dental materials, and a system including a device and a mixer. Further the invention relates to a device for mixing and dispensing dental materials.

BACKGROUND ART

Dental materials, particularly dental impression materials, are often provided as two- or multi-component materials that are separately stored but mixed together just before use. In recent years, devices have been developed which provide for automatic mixing and dispensing of two-component dental materials. An exemplary device for mixing and dispensing a dental impression material is for example available under the designation 3M™ ESPE™ Pentamix™ from 3M ESPE AG, Germany. Appropriate packages have been developed which contain the individual components of the material and allow the dental materials to be dispensed from such a mixing and dispensing device.

Typically the material components are simultaneously supplied from such a package through a mixer. The mixer typically mixes continuously supplied components as they flow through the mixer, and provides the mixture from an outlet. Some mixing and dispensing devices are configured for dynamically mixing of the components. Appropriate mixers typically have a moving part, for example a mixing rotor, for actively agitating the components while they are supplied through the mixer.

The mixed components in many cases are adapted to chemically react with one another to form a hardenable material. A used mixer may therefore be blocked by the hardened material a time after the mixing and dispensing is discontinued. Therefore mixers used with mixing and dispensing devices as mentioned are therefore generally exchangeable and often disposable parts. Dentists and their assistants may have to remove and replace mixers several times each day.

An example of a mixing and dispensing device and a dynamic mixer is disclosed in WO 2007/106701. The device has a drive shaft for driving a mixer. The mixer is placeable on the drive shaft in two positions to facilitate placement of the mixer on the drive shaft.

EP1458467 discloses a device for mixing of two components to form a dental compound. The device has a mixer with inlet receptacles for the components and an outlet receptacle for the mixed compound. The device also has a mixing element that is disposed in the mixer and propelled around a longitudinal axis. The mixer has a coupling section with two coupling receptacles for connecting with two dispensing openings of a device for dispensing the two paste-like compounds. The mixer further has a coupling receptacle for coupling with a driving bar of the device.

Although a variety of different mixing and dispensing device and mixers are on the market there is still a need for solutions that helps providing improved handling for a user, and that are relatively inexpensive.

SUMMARY OF THE INVENTION

A first aspect of the invention relates to a mixer for mixing at least two-components of a dental material, and a second aspect of the invention relates to a device for dispensing at least two components of a dental material. Thus the invention concerns two inter-related entities which can alone or both implement the invention although in the following certain features may be described in context of a particular entity only.

According to the first aspect of the invention relating to the mixer, the mixer preferably comprises a mixing chamber, at least two inlets for the components that are connected to the mixing chamber, and an outlet for dispensing a mixture from the components. The mixer, preferably disposed in the mixing chamber, comprises further a mixing rotor which is rotatable about a rotation axis.

The invention of the first aspect can further be implemented within two alternative embodiments. In a first alternative embodiment related to the first aspect of the invention the mixing rotor has a coupling receptacle for coupling with a coupling plug for driving the mixing rotor. In a second alternative embodiment related the first aspect of the invention the mixing rotor has a coupling plug for coupling with a coupling receptacle for driving the mixing rotor.

According to the second aspect of the invention relating to the device, the device preferably is adapted to receive the components, for example in a container or in individual containers. The device may have at least one plunger for advancing the components toward an outlet or outlets of the container(s). The device may further be adapted to receive a mixer for mixing the components. The container(s) and/or the device may be adapted to connect a mixing chamber of the mixer with the outlet(s) of the container(s) such that the components can be advanced from the container(s) into the mixing chamber. Further the device has a drive shaft for driving a mixing rotor of the mixer. The drive shaft is rotatable about a rotation axis.

The second aspect of the invention provides for a third and a fourth alternative embodiment of the invention. In the third alternative embodiment related to the second aspect of the invention the drive shaft has a coupling plug for coupling with a coupling receptacle of the mixing rotor. In the fourth alternative embodiment related to the second aspect of the invention the drive shaft has a coupling receptacle for coupling with a coupling plug of the mixing rotor.

Therefore this specification relates to four alternative embodiments each of which implements the invention, whereby certain features present in one embodiment may correspondingly be used in any other embodiment.

In the first and the fourth embodiments the coupling receptacle is defined by an inner surface around the rotation axis. Further the coupling receptacle comprises at least one guiding ridge that protrudes radially inwardly relative to an outer perimeter of the inner surface. The guiding ridge having a vertex oriented radially inwardly relative to the outer perimeter of the inner surface. The vertex extends along a path which has a tangent that is inclined relative to the rotation axis and a normal of the rotation axis.

The guiding ridge preferably corresponds to an elongated structure that has a convex cross-sectional shape with the vertex of the ridge extending along the apex of the convex cross-sectional shape. Thus the vertex preferably forms a continuous line.

In the second and the third embodiments the coupling plug is defined by an outer surface around the rotation axis. Further the coupling plug comprises at least one guiding ridge that protrudes radially outwardly relative to an inner perimeter of the outer surface. The guiding ridge having a vertex oriented radially outwardly relative to the inner perimeter of the outer surface. The vertex extends along a path which has a tangent that is inclined relative to the rotation axis and a normal of the rotation axis.

The invention may generally facilitate mounting of the mixer to a dispensing device. In particular the invention may allow for easy mounting of the mixer to a rotating drive shaft of a mixing device. The invention may for example provide for the mixer and the drive shaft to automatically move axially toward one another during the mixer and the rotating drive shaft are mated. Further the invention may allow for mounting of the mixer to a non-rotating drive shaft of a mixing device without rotationally aligning one to the other. The invention may accordingly provide for the mixer and the drive shaft to automatically align to one another during the mixer and the non-rotating drive shaft are mated. The invention may further help increasing the reliability in operation of the mixer in combination with the device. As an advantage the invention can be implemented relatively easily and at relatively low cost, for example without the need to include additional parts to either the mixer or the device, or both. It may also be advantageous that mixers of the invention may be used with devices that are already used in the market. For example the invention may be implemented in new mixers. Because mixers are typically consumables a user can be easily retrofitted with mixers of the invention. A user thus is not required to change the device, for example. Further the user can use up conventional mixers which may be present in the inventory.

In the following the invention is described by reference to the first embodiment of the first aspect of the invention. However the features mentioned may be used for other embodiments of the first or second aspects of the invention. The skilled person will understand that certain relationships between features as described for the coupling receptacle must be transposed, for example inverted, for use at the coupling plug to achieve similar effects of the invention.

In one embodiment the vertex of the guiding ridge of the coupling receptacle forms a minimum distance of the inner surface relative to the rotation axis of the mixing rotor. Further this minimum distance preferably increases toward a coupling end of the receptacle. The coupling end of the receptacle preferably corresponds to an end of the receptacle which the coupling plug penetrates first during mating of the receptacle and the plug. Therefore the guiding ridge may form a structure in the receptacle which, at least with the vertex of the guiding ridge, extends away from the rotation axis in a direction toward the coupling end. The inner perimeter of the cross-section of the receptacle may thus increase toward the coupling end.

In another embodiment the vertex of the guiding ridge of the coupling plug forms a maximum distance of the outer surface relative to the rotation axis. Further this maximum distance preferably decreases toward a coupling end of the plug. The coupling end of the plug preferably corresponds to an end of the plug which the coupling receptacle surrounds first during mating of the receptacle and the plug. Therefore the guiding ridge may form a structure on the plug which approximates the rotation axis in a direction toward the coupling end. The outer perimeter of the cross-section of the plug may thus decrease toward the coupling end. The receptacle and/or the plug may further have a chamfer adjacent the coupling end. Therefore the receptacle may generally widen toward the coupling end and the plug may generally taper toward the coupling end so that mating with a respective plug or receptacle may be facilitated.

In one embodiment the guiding ridge, in particular the vertex of the guiding ridge, extends generally straight. In this embodiment the guiding ridge may be formed between two planes. Such two planes may for example in combination form a step in the coupling receptacle. The coupling receptacle may therefore have a first plane which is approximately parallel to the rotation axis of the mixer, and a second plane which is inclined relative to the rotation axis of the mixing rotor and relative to a normal of the rotation axis of the mixing rotor. The first and second planes may in combination form an included angle relative to one another of between 0 degrees and 180 degrees, more preferably of between about 45 degrees and about 135 degrees. Further the second plane may be inclined relative to the rotation axis at an angle of between 0 and 90 degrees, more preferably between 30 and 60 degrees. The so formed guiding ridge, when mated with a cooperating coupling plug of a drive shaft, may facilitate mounting of the mixer to the drive shaft.

In a further embodiment the guiding ridge, in particular the vertex, extends substantially along a conical helix. This may be achieved in that the guiding ridge is formed between a helicoid surface and a plane. The helicoid surface and the plane may in combination form a step that has an included angle of between 0 degrees and 180 degrees, more preferably of between about 90 degrees and 180 degrees. Further the plane may be generally parallel relative to the rotation axis. A helical guiding ridge may be particularly advantageous for mounting a mixer onto a rotating drive shaft. Further this embodiment may provide for a line contact between the helicoid surface and a cooperating flat surface of a mated coupling plug. Thus wear of the coupling plug and/or the couping receptacle may be minimized.

In one embodiment the mixer, in particular the coupling receptacle or coupling plug, has a plurality of guiding ridges. Preferably the guiding ridges are substantially equally distributed around the rotation axis. For cooperation with a hexagonal coupling plug the coupling receptacle may have three or six guiding ridges that are distributed (for example evenly or generally evenly distributed) from each other around the rotation axis. This may provide for concentrically guiding the mixer relative to the drive shaft and thus may further facilitate mounting of the mixer on the drive shaft. Further the free ends of the coupling receptacle or the coupling plug may have a circumferential radius or chamfer. This may additionally facilitate mounting of the mixer on the drive shaft The mixer, in particular the coupling receptacle, may comprise an engagement section and an infeed section. The infeed section may provide for easy mounting of the mixer on a drive shaft, and the engagement section may allow for transmission of a torque that is sufficient to drive the mixing rotor in use for mixing the components. Accordingly the infeed section is preferably arranged adjacent the coupling end, and between the engagement section and the coupling end. Preferably the infeed and engagement sections are arranged adjacent, preferably adjoining Preferably the infeed section comprises the guiding ridges according to the invention, and thus may facilitate mounting of the mixer. The engagement section may comprise a positively engageable cross-section, and thus may be adapted to tightly fit with a correspondingly shaped coupling plug for transmission of torque. A profile that can be positively engaged may have any non-circular shape. Examples of positively engageable cross-sections include triangular, rectangular, and hexagonal cross-sections. Further a positively engageable cross-section may resemble or correspond to a segment of a circle.

In an example the engagement section may have a polygonal, for example hexagonal, cross-section having an outer perimeter around the rotation axis. The infeed section may have surface portions extending on or radially outside a perimeter that corresponds in size and is concentric to the outer perimeter of the engagement section. The infeed section further may have guiding ridges that protrude at least with their vertexes inside a perimeter that corresponds in size and is concentric to the outer perimeter of the engagement section. A particular embodiment may therefore have an engagement section having a generally hexagonal cross-section, and an infeed section having a cross-sectional profile formed of a hybrid of a hexagon and a circle. Such a profile may for example axially extend between a circle and a hexagon and may radially have a profile which comprises elements of a hexagon and elements of a circle. The person skilled in the art will recognize that other embodiments are possible. Generally any hybrid of a positively engageable profile and a second profile that is equal or greater than an outer perimeter of this positively engageable profile may be used for the receptacle. Accordingly any hybrid of a positively engageable profile and a second profile that is equal or smaller than an inner perimeter of the positively engageable profile may be used for the coupling plug.

Another embodiment comprises the mixer of the invention in combination with a device for dispensing at least two-components of a dental material, the device comprising a drive for driving the mixing rotor of a mixer. For example the mixer of the invention may be used with a mixing and dispensing device which is available under the designation 3M™ ESPE™ Pentamix™, from 3M ESPE AG, Germany. Further the mixer of the invention may be used with other device having an appropriate interface to the mixer. Therefore the invention may be easily used with devices that are already in the market.

One embodiment comprises a device according to the invention and a mixer, for example a conventional mixer. The conventional mixer may comprise a mixing rotor for mixing the components. The mixing rotor may be arranged in a mixing chamber which has inlets for receiving the components and an outlet for dispensing the mixture of the components. New devices may for example be implemented with the invention so that a user can take advantage of the invention also with conventional mixers.

Another embodiment comprises the device of the invention in combination with a mixer of the invention. This allows the use of the device of the invention with conventional mixers and with mixers according to the invention. Thus the invention may also be advantageous because it may allow various combinations of conventional or inventive mixers with conventional or inventive devices.

DETAILED DESCRIPTION OF THE INVENTION

Figure 1:
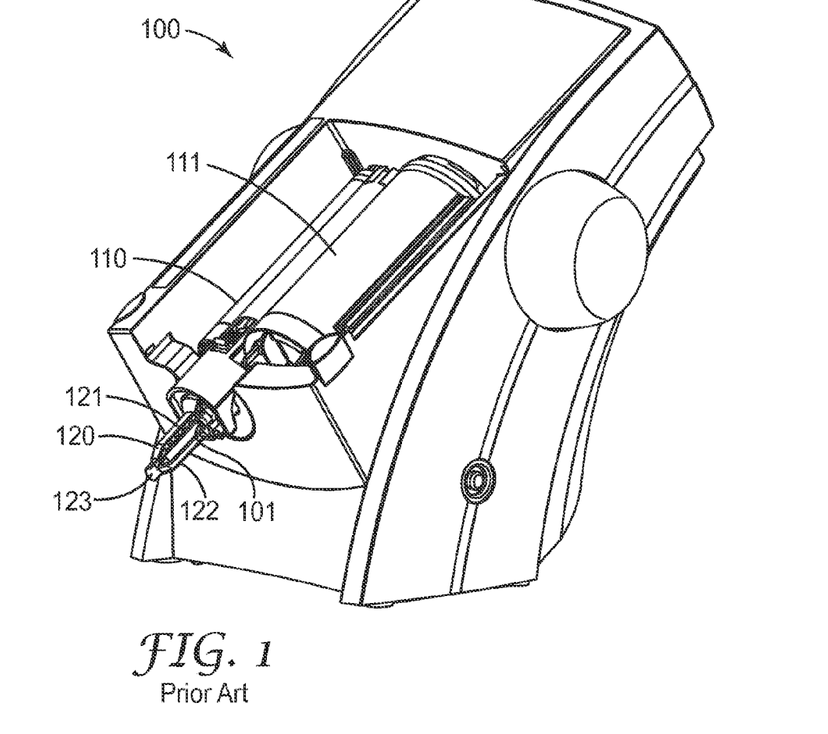
FIG. 1 is a perspective view of a dental mixing and dispensing device as it may be used with the present invention.

FIG. 1 shows a device 100 for mixing and dispensing of dental materials. A similar device is available under the designation 3M™ ESPE™ Pentamix™ from 3M ESPE AG, Germany. The device 100 holds two components of a dental material in containers 110, 111. A mixer 120 for mixing the two components is attached to the device 100. The mixer 120 has a mixing chamber formed between a rotatable mixing rotor 121 and a mixer housing 122. The mixer is connected with the containers 110, 111 such that the individual components can flow into the mixing chamber where they can be mixed by help of rotating the mixing rotor 121. The mixture can exit through an outlet 123 of the mixer 120. The components can be advanced toward the mixer 120 by pistons (not shown) of the device 100. The mixing rotor 121 is connected to a drive shaft 101 of the device 100 so that the mixing rotor 121 can be rotated by the device. The device shown may be used to mix and dispense a hardenable dental impression material, for example. The mixed material may be used to fill a dental tray which is then placed into a patient's mouth to take a dental impression. The mixer is attached replaceably at the device 100. Therefore when the mixed material hardens and thus blocks the mixer the used mixer may be replaced by an unused mixer for the next use of the device. The device 100 and the mixer 120 therefore have cooperating couplings which allow the mixer to be attached and detached from the device, for example by a user. In the example shown cooperating couplings are arranged at the drive shaft 101 and the mixing rotor 121 for connecting the mixing rotor 121 to the drive shaft 101. Further cooperative couplings are arranged at the mixer to connect the mixing chamber and the containers.

Figure 2:
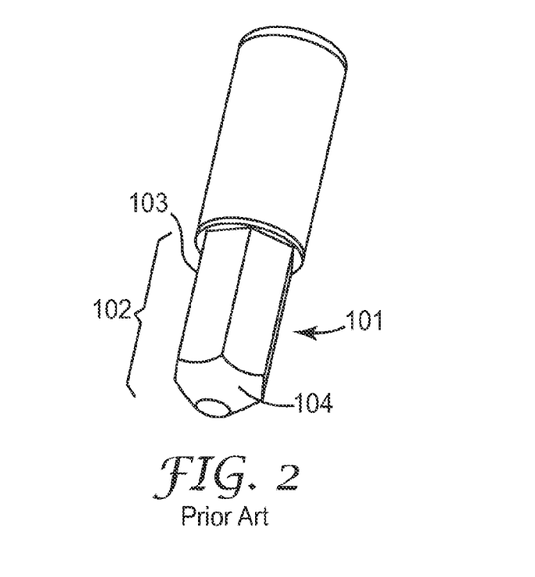
FIG. 2 is a perspective view of a drive shaft for driving a mixer of the dental mixing and dispensing device shown in FIG. 1.

FIG. 2 shows in detail an end of the drive shaft 101. The drive shaft 101 has a drive shaft coupling with a coupling plug 102. The coupling plug 102 of the drive shaft coupling comprises an engagement section 103 and a chamfer 104. The engagement section 103 in the example has a hexagonal cross-section. Accordingly a mixer (not shown) that may be used with the drive shaft shown may have a mixer coupling with a corresponding hexagonal opening.

Figure 3:
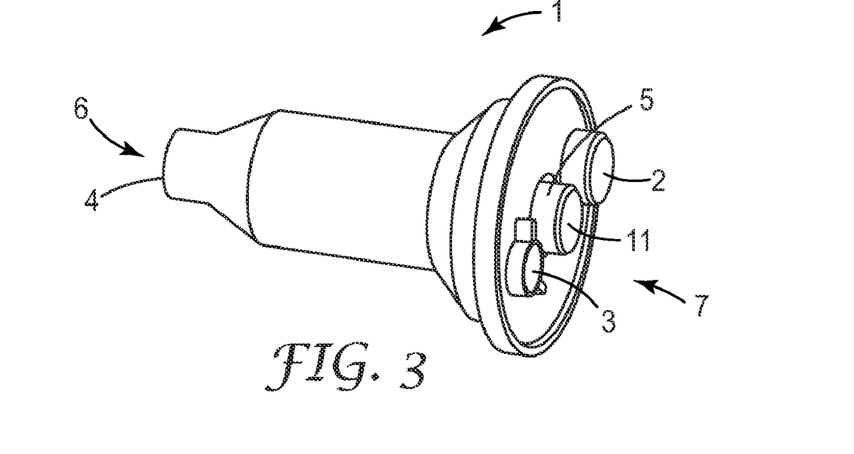
FIG. 3 is a perspective view of a mixer according to an embodiment of the invention.

FIG. 3 shows a mixer 1 according to the present invention. The mixer 1 has a coupling end 7 and opposite thereof a dispensing end 6. The mixer 1 has inlets 2, 3 at the coupling end 7, and an outlet 4 at the coupling end 7. The mixer 1 comprises a mixing rotor 5 which at the coupling end 7 has a mixer coupling with a coupling receptacle 11.

The coupling receptacle 11 may be used to connect the mixing rotor 5 to an drive shaft coupling of a mixing and dispensing device, for example one as shown in FIG. 1. Accordingly the coupling end 7 of the mixer is the end facing the drive shaft when the mixer is mounted to the drive shaft. The mixer inlets 2, 3 may be used to connect the mixer 1 to containers holding material to be mixed, for example. Therefore the mixer inlets may be adapted to form couplings for cooperation with couplings at the containers. Different embodiments for the couplings are possible. A mixer inlet may, for example, be formed by a plug for fitting with a receptacle in a nozzle of a container. Further an inlet may be formed by a receptacle for receiving a plug formed at a nozzle, for example. Other configurations are possible as appropriate, though. In the example shown a first mixer inlet 2 is formed as a generally cylindrical plug, and a second mixer inlet 3 is formed as generally cylindrical receptacle.

Figure 4:
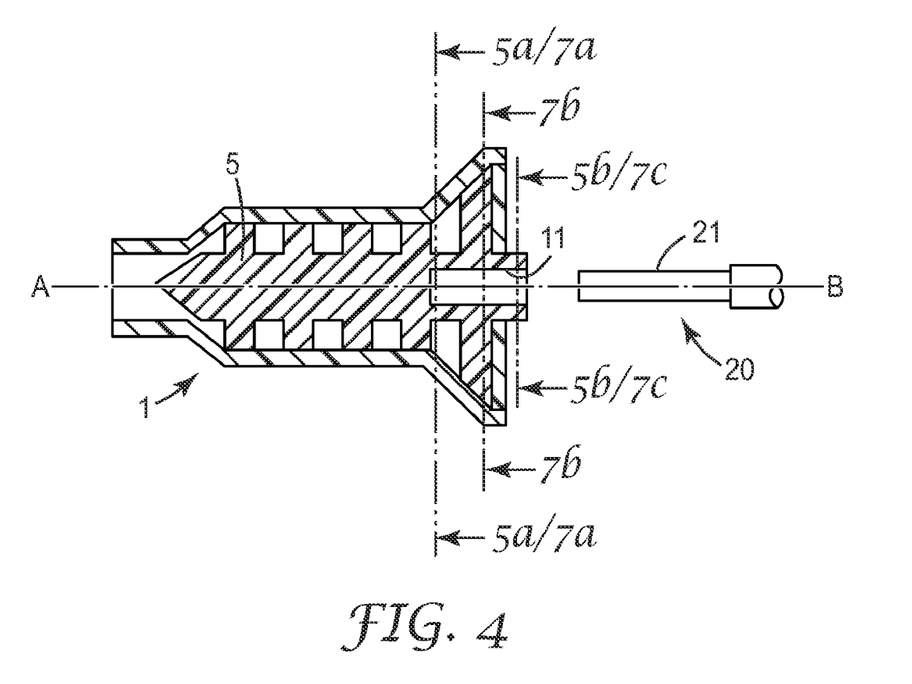
FIG. 4 is a cross-sectional view of a mixer vis-à-vis a drive shaft according to an embodiment of the invention.

FIG. 4 shows a cross-section of the mixer 1 and a drive shaft 20. The drive shaft 20 at a front end has a drive shaft coupling with a coupling plug 21. The coupling receptacle 11 of the mixing rotor 5 and the coupling plug 21 of the drive shaft 20 are adapted for mating with one another. In particular the coupling receptacle 11 and the coupling plug 21 are adapted for positive engagement with one another. For better clarity the following examples generally refer to a mixer comprising the coupling receptacle, and the drive shaft comprising the coupling plug. However the person skilled in the art will recognize that likewise the plug and receptacle may be interchanged so that the coupling receptacle is arranged at the drive shaft and the corresponding coupling plug is arranged at the mixing rotor. Therefore the coupling plug may generally be a part of the mixer or the drive shaft and accordingly also the coupling receptacle may be generally a part of the mixer or the drive shaft.

The coupling receptacle 11 of the mixer 1 extends along a rotation axis A of the mixer 1, and the coupling plug 21 of the drive shaft extends along a rotation axis B of the drive shaft 20. Both the coupling receptacle 11 and the coupling plug 21 have a cross-sectional profile that is shaped such that it can be positively engaged. In particular the cross-sectional profile of the coupling receptacle and/or the coupling plug may be hexagonal (as illustrated in FIG. 2 for example). The skilled person will however recognize that other positively engageable profiles are possible, including for example triangular, rectangular, or any other polygonal shape. Exemplary polygonal shapes also comprise star shapes and cross shapes. Combinations of different shapes are possible.

The coupling receptacle 11 of the example at least over a distance axially along the rotation axis of the mixing rotor varies in profile. Thus the coupling receptacle may have different profiles at different axial positions of the rotation axis. The views in FIGS. 5a and 5b, for example, illustrate exemplary profiles of the coupling receptacle 11 at different axial positions on the rotation axis of the mixing rotor as indicated in FIG. 4. The design of the coupling receptacle 11 according to the invention is preferably adapted to facilitate connecting the mixer and the drive shaft. In particular the design of the coupling receptacle preferably allows relatively high tolerances in rotational alignment between the mixer and the drive shaft for mounting the mixer onto the drive shaft. Further the coupling receptacle preferably helps ensuring proper alignment in the finally mounted position of the mixer on the drive shaft. This will be explained in more detail in the following.

Figure 5A:
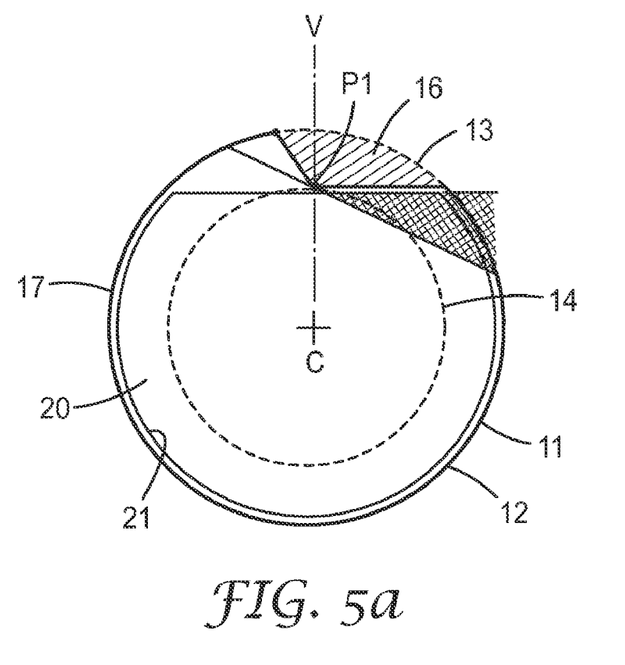
FIGS. 5a, 5b are cross-sectional views at different axial positions of a coupling according to an embodiment of the invention.

FIG. 5a shows a cross-section of the coupling receptacle 11 at a first axial position on the rotation axis of the mixing rotor (indicated in FIG. 4). The coupling receptacle 11 is defined by an inner surface 17 extending radially around the rotation axis of the mixing rotor. In the Figure the rotation axis of the mixing rotor corresponds to the center C. The inner surface 17 in the example forms a guiding ridge 16 which protrudes radially inwardly relative to an outer perimeter 13 of the inner surface 17. Thus at the first axial position the inner surface 17 has a first profile 12 as shown in FIG. 5a. The first profile 12 extends between the outer perimeter 13 and a first inner perimeter 14. The outer and inner perimeters 13, 14 are preferably substantially concentric to the rotation axis of the mixing rotor. The guiding ridge 16 forms a vertex at a first point P1 on the first inner perimeter 14. The first point P1 in FIG. 5a is further located on a vertical V through the center C. The position of the first point P1 can be defined in polar coordinates in a polar coordinate system having its pole in center C and its polar axis along the vertical. Therefore the first point P1 has a radius R1 and an angle T1, wherein in the example the angle T1 (not indicated) is zero.

Figure 5B:
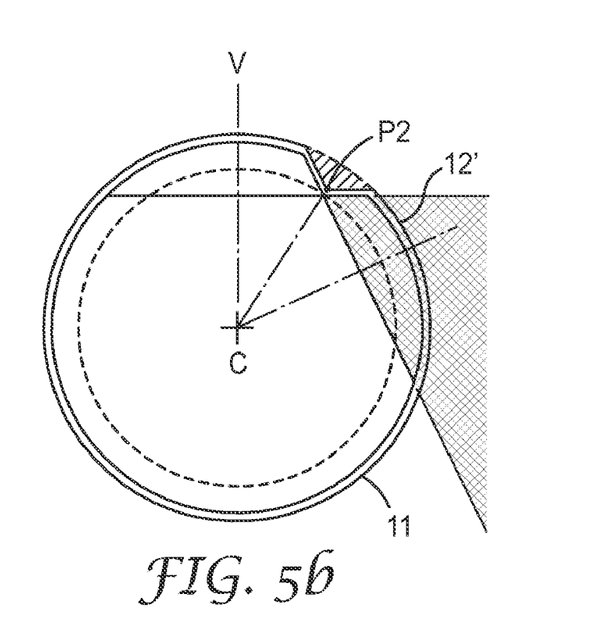

FIG. 5b shows a second profile 12' of the coupling receptacle 11. The second receptacle profile 12' corresponds to the cross-sectional shape of the inner surface 17 at a second axial position on the rotation axis of the mixing rotor (indicated in FIG. 4). The second axial position is located further toward the coupling end 7 of the mixer. The second profile 12' is different from the first profile 12. In particular the second profile has a second inner perimeter 14' which is greater than the first inner perimeter 14. Further the vertex of the guiding ridge 16 is positioned at a second point P2 offset from the position of the first point P1. The position of the point P2 in the same coordinate system as referred to under the description of FIG. 5a is different in radius and angle relative to the first point P1 shown in FIG. 5a. The point P2 in particular has a radius R2 which is greater than the radius R1, and further has an angle T2 that is different from the angle T1.

FIGS. 5a and 5b further illustrate the cross-sectional shape of the coupling plug 21 of the drive shaft 20 relative to the first and second profiles 12, 12'. The coupling plug 21 extends substantially cylindrical along the rotation axis of the drive shaft, but has a radial flat. The rotation axis of the drive shaft extends about perpendicularly to the plane of the Figures through the center C. In FIG. 5a the coupling plug 21 is inserted in the coupling receptacle 11 up to the first axial position of the profile. In this position there is relatively little rotational freedom or play (indicated by the cross-hatched area) between the coupling plug 21 and the coupling receptacle 11. Further the drive shaft when fully mounted to the mixing rotor preferably positively engages with the mixing rotor such that relatively little rotational play between the drive shaft and the mixing rotor exists. In the situation shown in FIG. 5b the rotational play (see cross-hatched area) between the drive shaft and the mixing rotor is higher than in the situation shown in FIG. 5a. FIG. 5b illustrates a situation in which the coupling plug is only partially inserted in the coupling receptacle up to the second axial position. Thus adjacent the coupling end the coupling receptacle allows for a relatively high rotational play between the plug and the receptacle. Therefore the coupling receptacle accepts for mating with the coupling plug within a relatively large continuous range of rotational positions. This is in contrast to a coupling plug and a coupling receptacle having similar cross-sectional shapes. A coupling plug and a coupling receptacle that are similarly shaped typically allow mating only in substantially one position or several discrete positions. The invention therefore may facilitate mounting of the mixer to the drive shaft.

Further the coupling receptacle 11 varies in profile over the distance between the first and second axial position. In particular the vertex of the guiding ridge 16 extends along a path which has a tangent that is inclined to the rotation axis of the mixing rotor as well as to a normal of the rotation axis of the mixing rotor. Preferably the vertex of the guiding ridge 16 extends continuously along the path. In the example shown in FIG. 5a, 5b the vertex of the guiding ridge may extend along a generally straight line that is inclined to the rotation axis and to a normal of the rotation axis. Further the vertex of the guiding ridge may extend on a helical curve around the rotation axis, for example a conical helical curve, which has a tangent inclined relative to the rotation axis and a normal thereof. The vertex of the guiding ridge may further extend along other curves like parabolic curves, cubic curves or curves following or resembling higher order polynominals. The path of the vertex of the guiding ridge may also be defined by polar coordinates which describe the position of every point on the vertex in a three-dimensional space around the rotation axis. For example the coordinates of the vertex may vary continuously between the first and second points P1, P2. In particular the radius and the angle of the vertex may continuously increase (or decrease) between the first and second points P1, P2.

During mating of the mixer with a rotating drive shaft the guiding ridge may therefore provide for an axial feed that urges the mixer toward the drive shaft. Thus the mixer may be automatically advanced onto the drive shaft, and proper mounting of the mixer may be facilitated. This principle is further explained in the example shown FIG. 6.

The guiding ridge may be arranged at the mixer and/or the drive shaft such that the axial feed urging the mixer and the drive shaft toward one another is provided when the drive shaft rotates in a mixing direction that is appropriate to drive the mixing rotor of the mixer for mixing material. The device may further have a mode in which the drive shaft rotates reverse to the mixing direction. Therefore the guiding ridge may provide for an axial feed that urges the mixer and the drive shaft away from one another when the drive shaft rotates in a direction reverse to the mixing direction. Further the mixer and/or the device may have two different guiding ridges. One guiding ridge may provide for an axial feed urging the mixer and the drive toward one another when the drive shaft rotates in the mixing direction. Another guiding ridge may provide for an axial feed urging the mixer and the drive away from one another when the drive shaft rotates in the reverse of the mixing direction. Those two different guiding ridges may have different dimensions and or may be arranged such that the vertexes follow different paths. Further multiple of such two different guiding ridges may be present, for example generally evenly distributed around the rotation axis.

Figure 6:
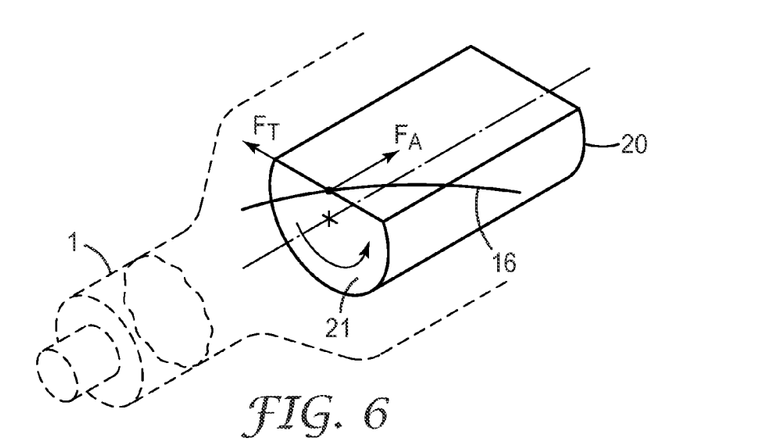
FIG. 6 is a perspective view illustrating forces preferably occurring in cooperation of connected couplings one of which is a coupling according to an embodiment of the invention.

FIG. 6 illustrates a situation in which a mixer 1 is moved, for example pushed, on a rotating drive shaft 20. The mixer 1 is not shown in detail, but a guiding ridge 16 of the coupling receptacle of the mixer 1 is shown in engagement with the coupling plug 21. Due to the rotation of the drive shaft 20 and the coupling plug cooperating with the guiding ridge 16 an axial force $F_A$ is applied to the mixing rotor of the mixer. Further a resulting tangential force $F_T$ is applied to the mixing rotor. Therefore the mixing rotor is urged for rotational and axial movement. Mounting of a mixer onto a rotating drive shaft may thus be facilitated.

Further, for example in case the drive shaft does not rotate, the mixer when moved onto the drive shaft may cause the coupling plug and the coupling receptacle to automatically align with one anther. This is because of the guiding ridge 16 in cooperation with the shape of the coupling plug 21 may provide for a tangential force $F_T$ resulting in a rotation between the mixing rotor and the drive shaft when the mixer is axially forced onto the drive shaft. Therefore also mounting of a mixer onto a non-rotating drive shaft may be facilitated.

The person skilled in the art will recognize that other structures instead of a continuous guiding ridge may provide a similar or equivalent effect. For example a plurality of discrete protrusions or any other appropriate structure along a path or curve may be used.

Figure 7A:
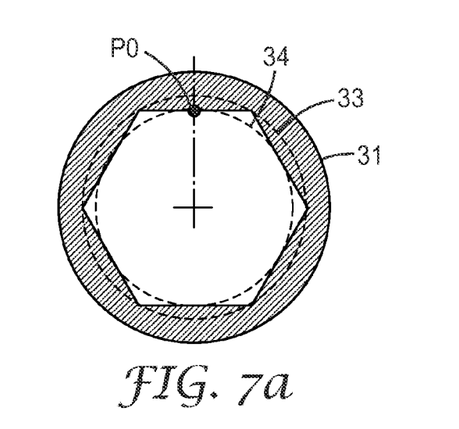
FIGS. 7a-7c are cross-sectional views of a further coupling according to an embodiment of the invention.
Figure 7B:
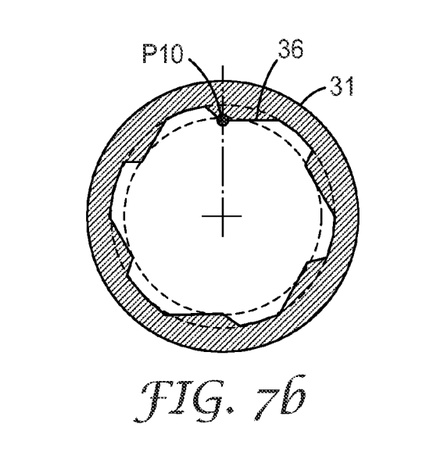
Figure 7C:
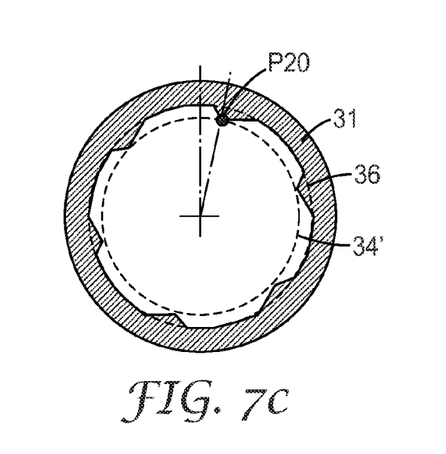

FIGS. 7a-7c illustrate an example of a coupling receptacle 31 which is adapted for cooperation with a hexagonal coupling plug (not shown). In FIG. 7a a cross-section of the receptacle is shown at the first axial position as indicated in FIG. 4. The first profile is generally hexagonal and extends between an outer perimeter 33 and a first inner perimeter 34. The first profile of FIG. 7a may be generally constant along the rotation axis of the mixing rotor up to the second axial position (see FIG. 4). Therefore an engagement section may be formed which has a generally constant hexagonal profile over its lengths. Such an engagement section may allow for transmission of a relatively high torque between the coupling receptacle and the coupling plug because the coupling plug and the coupling receptacle may fit relatively firmly over a certain length with one other.

FIG. 7b shows a second profile of the coupling receptacle 31 at the second axial position. The second profile also extends between the outer perimeter 33 and the inner perimeter 34. The section of the coupling receptacle between the first and second axial positions may, as mentioned, extend with a generally constant profile.

Between the second and third axial positions on the rotation axis of the mixing rotor (FIGS. 7b, 7c respectively) the coupling receptacle 31 has an infeed section. The infeed section varies in profile from the profile shown in FIG. 7b toward the profile shown in FIG. 7c. In particular the infeed section has a guiding ridge 36 that extends radially inwardly relative to the outer perimeter 33. The guiding ridge 36 has a vertex defining the first inner perimeter 34 (FIG. 7b) and the second inner perimeter 34' (FIG. 7c). The second inner perimeter 34' is greater than the first inner perimeter 34. Therefore, following the rotation axis from second toward the third axial position the guiding ridge extends away from the rotation axis. Further the polar coordinates (radius and angle) of the vertex varies continuously from the first Point P10 toward the second point P20 as described for FIGS. 5a and 5b. Thus the infeed section of the example shown in FIGS. 7b and 7c preferably provides for similar effects as described in the examples of FIGS. 5a and 5b respectively although the examples use differently shaped coupling receptacles. The person skilled in the art therefore will recognize that a variety of shapes, in particular but not exclusively polygonal shapes, may provide similar or equivalent effects.

Figure 8:
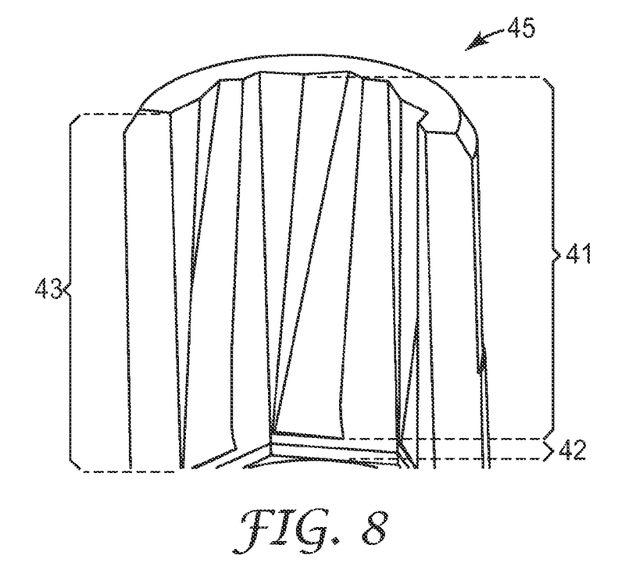
FIG. 8 is a perspective cross-sectional view of a mixing rotor having a coupling according to an embodiment of the invention.

FIG. 8 is a partial view of a mixing rotor 45. The mixing rotor 45 has a coupling receptacle 43 with an engagement section 42 and an infeed section 41. The engagement section 42 in the example has a generally hexagonal shaped cross-section, although other shapes allowing for positive engagement with an appropriately shaped coupling plug are possible. The coupling receptacle 43 with the engagement section 42 and the infeed section 41 generally corresponds to the embodiment of the examples of FIGS. 7b and 7c.

Figure 9:
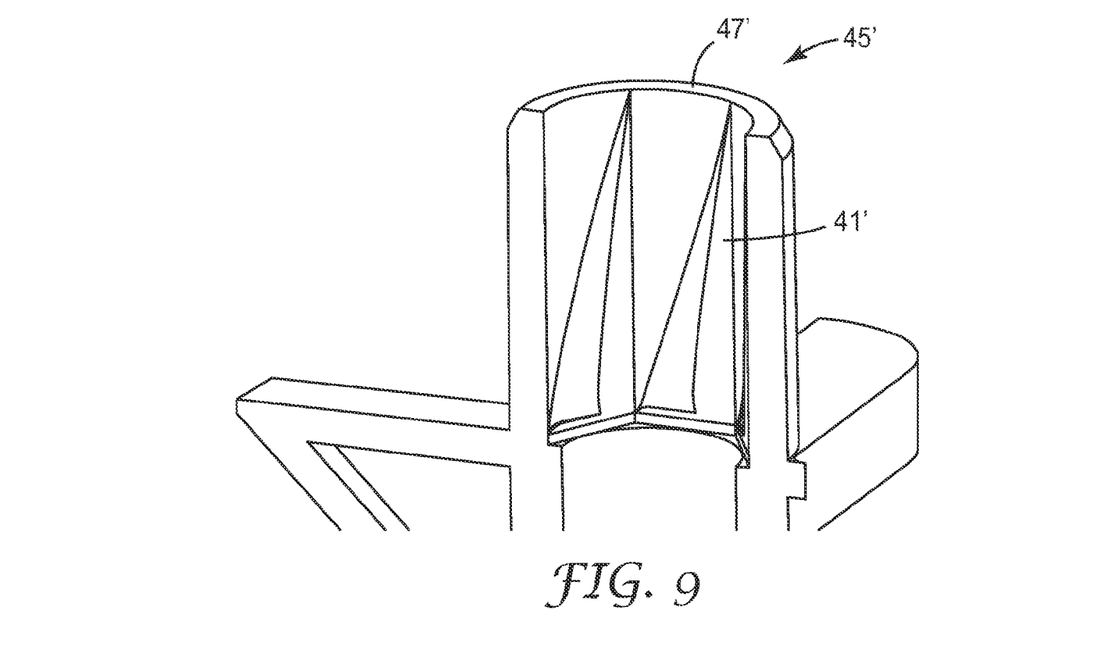
FIG. 9 is a perspective cross-sectional view of a mixing rotor having a coupling according to another embodiment of the invention.

FIG. 9 is a partial view of a mixing rotor 45' which also generally corresponds to the embodiments shown in FIGS. 7a-7c, but having an infeed section 41' having a generally circular shape at its open end 47'. Therefore the infeed section 41' may allow for mating with a drive shaft, for example a hexagonal drive shaft, at any rotational alignment of the mixer and the drive shaft relative to one another.

Figure 10:
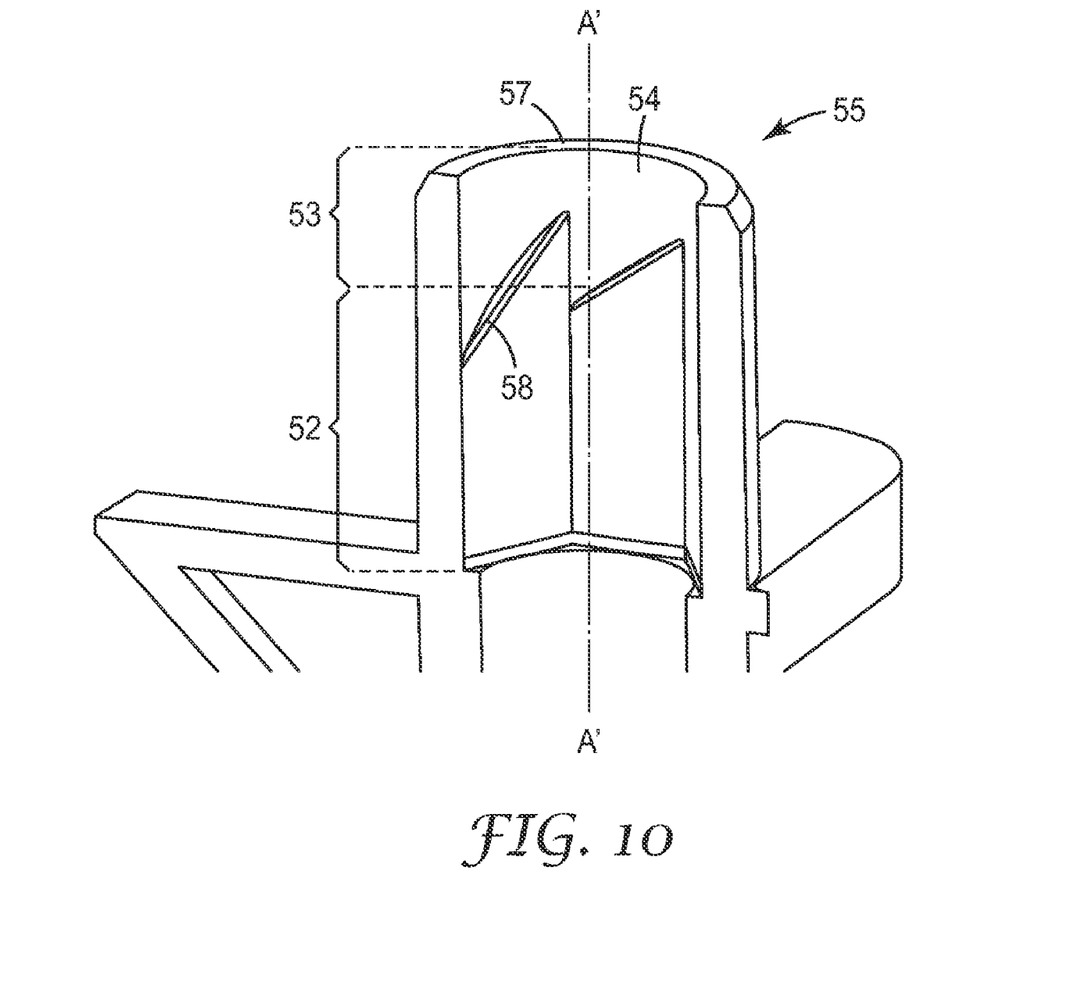
FIG. 10 is a perspective cross-sectional view of a mixing rotor having a coupling according to still another embodiment of the invention.

FIG. 10 is a partial view of a mixing rotor 55. The mixing rotor 55 has an engagement section 52 and an infeed section 53. In the example the engagement section 52 has a generally hexagonal profile over its length. The infeed section 53 has recessed areas 54 with respect to the hexagonal shape. Thus the remaining areas form guiding ridges 58. In particular the hexagonal shape is successively recessed toward the open end 57 of the coupling receptacle and merges into a circular shape. In the example shown the recesses extend radially outwardly relative to the rotation axis A' and may extend at least up to an outer perimeter of the hexagon. In other words the guiding ridges 58 protrude radially inwardly relative to the outer perimeter of the hexagon. The recessed hexagonal shape in the infeed section thus provides the infeed section with generally straight guiding ridges 58 that are inclined relative to the rotation axis and a normal thereto. The guiding ridges 58 preferably provide for automatic advancement of the mixer during mating the mixer with a hexagonal coupling plug of a drive shaft. Further the guiding ridges 58 preferably help providing for automatic rotational alignment between the mixing rotor and the drive shaft during mating. The circular shape adjacent the open end of the mixing rotor 55 preferably allows for mating with the drive shaft at any rotational alignment of the mixer and the drive shaft relative to one another. Therefore connecting of the mixer to the drive shaft may be facilitated.

In another example the shape of the vertex of the guiding ridge is defined by a mathematical function relative to a Cartesian coordinate system having an axis Z on the rotation axis of the mixing rotor or the rotation axis on the drive shaft. The Cartesian coordinate system further has an X axis and a Y axis perpendicularly on the Z axis and perpendicularly to each other.

A vertex lying on a cylinder surface with a radius r around the Z axis and reaching from the angle ($\phi$1 to the angle $\phi$2 may be defined by:

$X = r * \cos \phi$
$Y = r * \sin \phi$
$Z = p * \phi$ with $\phi$1 being smaller than $\phi$ being smaller than $\phi$2, and with p defining a constant pitch.

A vertex lying on a conical surface around the Z axis with a smaller radius r1 and a greater radius r2 and reaching from the angle $\phi$1 to the angle $\phi$2 may be defined by:

$X = r(\phi) * \cos \phi$
$Y = r(\phi) * \sin \phi$
$Z = p * \phi$ where $r(\phi 1) = r1$ and $r(\phi 2) = r2$, r1 being smaller than $r(\phi)$ being smaller than r2, and $r(\phi)$ being steadily increasing, and with p defining a constant pitch.

The person skilled in the art will be able to transpose the principles as described for the coupling receptacle to a coupling plug. The coupling receptacle may for example widen toward the opening, and a corresponding coupling plug would taper toward its front end (the end leading for mating with the mixer).

Example

It was tested whether a mixer according to the invention can automatically align during mating with a drive shaft that is rotationally misaligned by intension, although a user would typically rotationally align the mixer to the drive shaft. For the example a Pentamix™ 3 Mixing Device, available from 3M ESPE AG, Germany, was used. The Pentamix™ 3 Mixing Device has a hexagonal coupling plug at an end of the mixing shaft. The device was switched off, and the mixer was pushed onto the misaligned drive shaft without rotating the mixer. The test was repeated twenty times.

Result

The mixer in all twenty cases mated with the drive shaft correctly, and thereby caused the mixing rotor and the drive shaft to align with each other without the help of the user.

The invention claimed is:

1. A mixer for mixing at least two-components of a dental material, comprising:
a mixing rotor which is rotatable about a rotation axis;
the mixing rotor having a coupling receptacle for coupling with a coupling plug for driving the mixing rotor;
the coupling receptacle being defined by an inner surface around the rotation axis;
the coupling receptacle further comprising at least one guiding ridge that protrudes radially inwardly relative to an outer perimeter of the inner surface;
wherein the guiding ridge has a vertex oriented radially inwardly relative to the outer perimeter;
wherein the vertex extends along a path which has a tangent that is inclined relative to the rotation axis and a normal of the rotation axis.

2. A mixer for mixing at least two-components of a dental material, comprising:
a mixing rotor which is rotatable about a rotation axis;
the mixing rotor having a coupling plug for coupling with a coupling receptacle for driving the mixing rotor;
the coupling plug being defined by an outer surface around the rotation axis;
the coupling plug further comprising at least one guiding ridge that protrudes radially outwardly relative to an inner perimeter of the outer surface;
the guiding ridge has a vertex oriented radially outwardly relative to the inner perimeter,
wherein the vertex extends along a path which has a tangent that is inclined relative to the rotation axis and a normal of the rotation axis.

3. The mixer of claim 1, wherein the vertex of the guiding ridge forms a minimum distance of the surface relative to the rotation axis, and wherein the minimum distance increases toward an end of the receptacle which is adapted to receive the coupling plug.

4. The mixer of claim 2, wherein the vertex of the guiding ridge forms a maximum distance of the surface relative to the rotation axis, and wherein the maximum distance decreases toward an end of the plug which is adapted to be inserted in the coupling receptacle.

5. The mixer of claim 1 or 2, wherein the vertex extends generally straight.

6. The mixer of claim 1 or 2, wherein the vertex extends substantially along a conical helix.

7. The mixer of claim 1 or 2, having a plurality of guiding ridges.

8. The mixer of claim 1 or 2, in combination with a device for dispensing at least two-components of a dental material, the device comprising a drive for driving the mixing rotor of the mixer.

9. A device for dispensing at least two components of a dental material, comprising:
a drive shaft for driving a mixing rotor of a mixer for mixing the components; the drive shaft being rotatable about a rotation axis;
the drive shaft having a coupling plug for coupling with a coupling receptacle of the mixing rotor;

the coupling plug being formed by a surface around the rotation axis;

the coupling plug further comprising at least one guiding ridge that protrudes radially outwardly relative to an inner perimeter of the surface;

the guiding ridge has a vertex oriented radially outwardly relative to the inner perimeter, wherein the vertex extends along a path which has a tangent that is inclined relative to the rotation axis and a normal of the rotation axis.

10. A device for dispensing at least two components of a dental material, comprising:

a drive shaft for driving a mixing rotor of a mixer for mixing the components; the drive shaft being rotatable about a rotation axis;

the drive shaft having a coupling receptacle for coupling with a coupling plug of the mixing rotor;

the coupling receptacle further comprising at least one guiding ridge that protrudes radially inwardly relative to an outer perimeter of the surface;

wherein the guiding ridge has a vertex oriented radially inwardly relative to the outer perimeter;

wherein the vertex extends along a path which has a tangent that is inclined relative to the rotation axis and a normal of the rotation axis.

11. The device of claim 9 or 10, further comprising a mixer, the mixer comprising a mixing rotor for mixing the components.

\* \* \* \* \*